US008022096B2

(12) United States Patent
Jiaang et al.

(10) Patent No.: US 8,022,096 B2
(45) Date of Patent: *Sep. 20, 2011

(54) PYRROLIDINE DERIVATIVES

(75) Inventors: Weir-Torn Jiaang, Taichung (TW); Yu-Sheng Chao, Warren, NJ (US); Ting-Yueh Tsai, Tainan (TW); Tsu Hsu, Taipei (TW)

(73) Assignee: National Health Research Institutes, Miaoli County (TW)

( * ) Notice: Subject to any disclaimer, the term of this patent is extended or adjusted under 35 U.S.C. 154(b) by 120 days.

This patent is subject to a terminal disclaimer.

(21) Appl. No.: 12/392,590

(22) Filed: Feb. 25, 2009

(65) Prior Publication Data
US 2009/0227569 A1  Sep. 10, 2009

Related U.S. Application Data

(60) Provisional application No. 61/033,877, filed on Mar. 5, 2008.

(51) Int. Cl.
- *C07D 417/12* (2006.01)
- *C07D 413/12* (2006.01)
- *C07D 401/12* (2006.01)
- *C07D 403/12* (2006.01)
- *C07D 207/16* (2006.01)
- *A61K 31/541* (2006.01)
- *A61K 31/5377* (2006.01)
- *A61K 31/496* (2006.01)
- *A61K 31/454* (2006.01)
- *A61K 31/4439* (2006.01)
- *A61K 31/427* (2006.01)
- *A61K 31/4025* (2006.01)
- *A61K 31/40* (2006.01)

(52) U.S. Cl. ............ 514/422; 514/237.2; 514/343; 514/252.13; 514/371; 514/326; 514/227.8; 544/60; 544/141; 544/372; 546/208; 546/256; 546/279.1; 548/195; 548/200; 548/523; 548/540

(58) Field of Classification Search .......... 514/422, 514/237.2, 343, 252.13, 371, 326, 227.8; 544/60, 141, 372; 546/208, 256, 279.1; 548/195, 548/200, 523, 540
See application file for complete search history.

(56) References Cited

U.S. PATENT DOCUMENTS

| 5,852,007 A | 12/1998 | Chatterjee |
| 2005/0222222 A1 * | 10/2005 | Jiaang et al. ............... 514/365 |
| 2007/0093492 A1 | 4/2007 | Jiaang et al. |

FOREIGN PATENT DOCUMENTS

| EP | 1333025 | 8/2003 |
| EP | 1595833 | 11/2005 |
| WO | WO2003/037327 | 5/2003 |
| WO | WO2004/043940 | 5/2004 |
| WO | WO2004/067509 | 8/2004 |
| WO | WO2004/103993 | 12/2004 |

OTHER PUBLICATIONS

Tsu et al. J. Med. Chem. 2006, 49, 373-380.*
Patani et al. Chem. Rev. 1996, 96, 3147-3176.*
Fukushima et al. Bioorg. Med. Chem. 2004, 6053-6061.*
Haffner et al. Bioorg. Med. Chem. Lett. 2005, 5257-5261.*
Coumar et al. Bioorg. Med. Chem. Lett. 2007, 17, 1274-1279 (Dec. 12, 2006).*
Hughes et al., "NPV-DPP728 (1[[[2-[(5-Cyanopyridin-2-yl)amino]ethyl]amino]acetyl]2-cyano-(S)-pyrrolidine), a Slow-Binding Inhibitor of Dipeptidyl Peptidase IV," Biochemistry 38:11597-11603 (1999).
Villhauer et al., "1-[2-[(5-Cyanopyridin-2-yl)amino] ethylamino]acetyl-2-(S)-pyrrolidine-carbonitrile: A Potent, Selective, and Orally Bioavailable Dipeptidyl Peptidase IV Inhibitor with Antihyperglycemic Properties," J. Med. Chem. 45:2362-2365 (2002).
Villhauer et al., "1-[[(3-Hydroxy-1-adamantyl)amino]acetyl]-2-cyano-(s)-pyrrolidine: A Potent, Selective, and Orally Bioavailable Dipeptidyl Peptidase IV Inhibitor with Antihyperglycemic Properties," J. Med. Chem. 56:2774-2789 (2003).
Edmondson et al., "Discovery of Pitent and Selective Orally Bioavailable Beta-Substituted Phenyalanine Derived Dipeptidyl Peptidase IV Inhibitors," Bioorganic & Medicinal Chemistry Letters, 15(12):3048-3052, 2005.

* cited by examiner

*Primary Examiner* — Joseph Kosack
*Assistant Examiner* — Matthew Coughlin
(74) *Attorney, Agent, or Firm* — Occhiuti Rohlicek & Tsao LLP

(57) ABSTRACT

Pyrrolidine compounds described herein and methods for using them to inhibit dipeptidyl peptidase IV and treat Type II diabetes.

1 Claim, No Drawings

PYRROLIDINE DERIVATIVES

RELATED APPLICATION

This application claims priority to U.S. Provisional Application No. 61/033,877, filed on Mar. 5, 2008, the content of which is hereby incorporated by reference in its entirety.

BACKGROUND

Dipeptidyl peptidase IV (DPP-IV), a member of the prolyl peptidase family, cleaves certain dipeptides at the penultimate position from the amino termini of the proteins. It contributes to rapid degradation of glucagon-like peptide-1 (GLP-1), a gut hormone produced by intestinal endocrine L-cells in response to food ingestion. GLP-1 in turn inhibits glucagon secretion and stimulates glucose-dependent insulin release from the pancreas (Zander M, et al. *Lancet* 2002, 359: 824-830). It has been shown that inhibiting DPP-IV resulted in enhanced insulin secretion, reduced plasma glucose levels, and improved pancreatic β-cell function (Pederson R. A., et al. *Diabetes* 1998, 47: 1253-1258; and Ahren B, et al. *Diabetes Care* 2002, 25: 869-875). DPP-IV inhibitors are therefore potential drug candidates for Type II diabetes.

Recent studies indicate that DPP-IV inhibitors were potential inhibitors of dipeptidyl peptidase VIII (DPP-VIII), another member of the prolyl peptidase family, and that inhibition of DPP-VIII resulted in side effects, e.g., toxicity and thrombocytopenia (*Diabetes*, 2005, 54: 2988-2994). Thus, DPP-IV inhibitors, as Type II diabetes drug candidates, preferably possess little or no inhibitory activity against DPP-VIII.

SUMMARY

This invention is based on a surprising discovery that a group of pyrrolidine compounds inhibit DPP-IV.

One aspect of this invention relates to pyrrolidine compounds of formula (I) shown below:

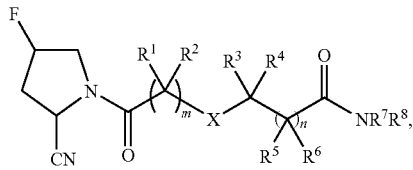

I wherein each of $R^1$, $R^2$, $R^3$, $R^4$, $R^5$, and $R^6$, independently, is H, halo, nitro, cyano, amino, hydroxy, alkyl, haloalkyl, alkoxy, aryloxy, aralkyl, cyclyl, heterocyclyl, aryl, or heteroaryl; $R^7$ is alkyl or heteroaryl, and $R^8$ is H or alkyl; or $R^7$ and $R^8$, together with the nitrogen atom to which they are attached, form a 3-10 membered monocyclic or bicyclic, saturated or unsaturated ring optionally substituted with halo, CN, $NO_2$, —OR', alkyl, aryl, heteroaryl, haloalkyl, hydroxyalkyl, alkoxyalkyl, —C(O)R', —SR', —S(O)R', —S(O)$_2$R', —NR'R'', —C(O)OR', —C(O)NR'R'', —OC(O)R', —NR'C (O)R'', —NR'C(O)OR'', or —R'C(O)NR''R'''; each of R', R'', and R''', independently, being H, alkyl, or aryl; each of m and n, independently, is 0, 1, 2, or 3; and X is $NR^a$, in which $R^a$ is H, alkyl, or aryl.

The compounds of formula (I) may further have one or more of the following features: X is NH; m is 1; n is 1; each of $R^1$ and $R^2$ is H; each of $R^3$ and $R^4$ is alkyl (e.g., methyl); each of $R^5$ and $R^6$ is H; and $R^7$ and $R^8$ is alkyl, $R^7$ and $R^8$, together with the nitrogen atom to which they are attached, form a 3-10 membered monocyclic or bicyclic, saturated or unsaturated ring optionally substituted with halo, CN, $NO_2$, —OR', alkyl, aryl, heteroaryl, haloalkyl, hydroxyalkyl, alkoxyalkyl, —C(O)R', —SR', —S(O)R', —S(O)$_2$R', —NR'R'', —C(O)OR', —C(O)NR'R'', —OC(O)R', —NR'C (O)R'', —NR'C(O)OR'', or —R'C(O)NR''R'''; each of R', R'', and R''', independently, being H, alkyl, or aryl. Examples of the just-mentioned ring include, but are not limited to, substituted or unsubstituted pyrrolidinyl, thiazolidinyl, piperidinyl, morpholinyl, thiomorpholinyl, piperizinyl, 1,2,3,6-tetrahydropyridinyl, isoindolinyl, and 7-azabicyclo[2.2.1]heptan-7-yl.

Another aspect of this invention relates to pyrrolidine compounds of formula (II) shown below:

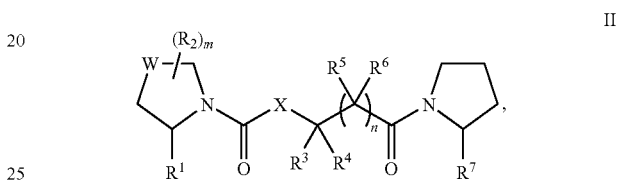

II wherein $R^1$ is H or CN; each of $R^2$, $R^3$, $R^4$, $R^5$ and $R^6$, independently, is H, halo, nitro, cyano, amino, hydroxy, alkyl, haloalkyl, hydroxyalkyl, alkoxyalkyl, alkoxy, aryloxy, aralkyl, cyclyl, heterocyclyl, aryl, or heteroaryl; $R^7$ is H, alkyl, hydroxyalkyl, or alkoxyalkyl; m is 0, 1, 2, 3, 4, or 5; n is 0, 1, or 2; W is $CR^aR^{a'}$, $NR^a$, O, or S, in which each of $R^a$ and $R^{a'}$, independently, is H, halogen, alkyl, or aryl; and X is O, S, or $CR^b(NR^{b'}R^{b''})$, in which each of $R^b$, $R^{b'}$, and $R^{b''}$, independently, is H, alkyl, or aryl.

The compounds of formula (I) may further have one or more of the following features: W is $CR^aR^{a'}$; $R^1$ is CN; X is $CH(NH_2)$; n is 1; each of $R^3$ and $R^4$, independently, is H or alkyl; each of $R^5$ and $R^6$ is H; and $R^7$ is alkyl (e.g., methyl), hydroxyalkyl (e.g., hydroxymethyl), or alkoxyalkyl (e.g., methoxymethyl).

Shown below are exemplary compounds of this invention:

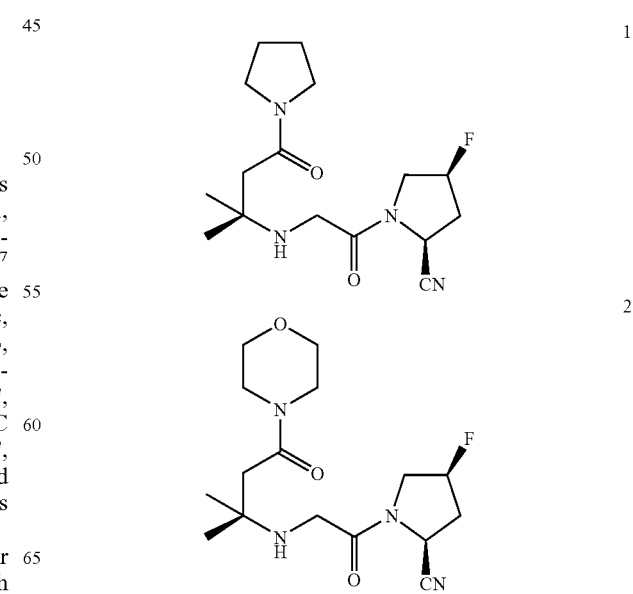

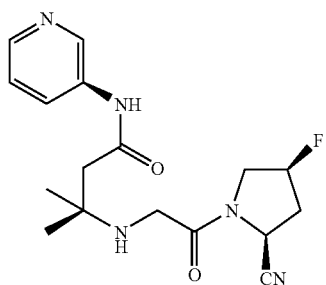
3
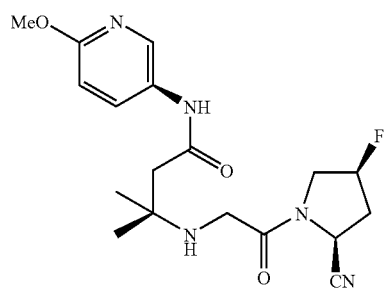
8
4
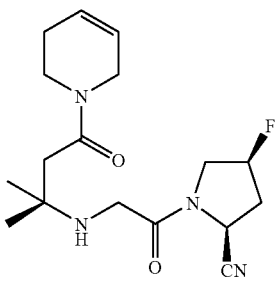
9
5
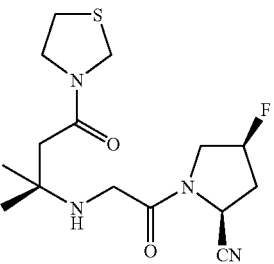
10
6
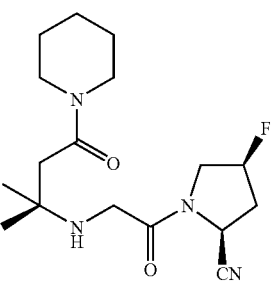
11
7
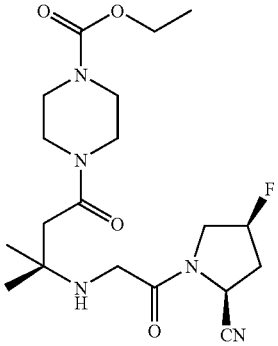
12

-continued
13
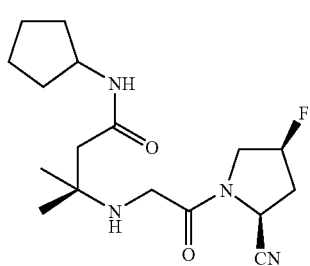
14
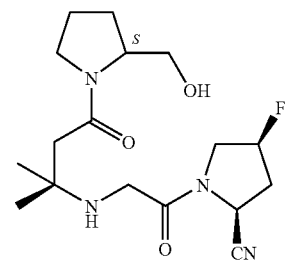
15
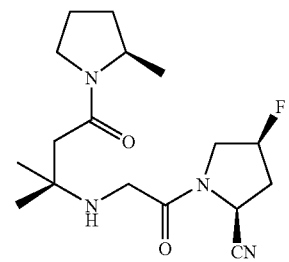
16
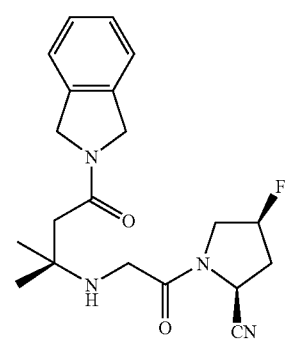
17
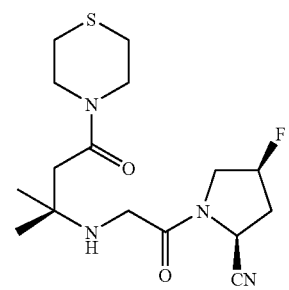
18
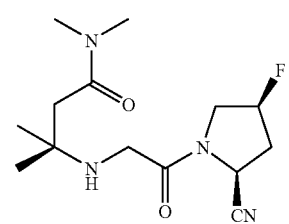
-continued
19
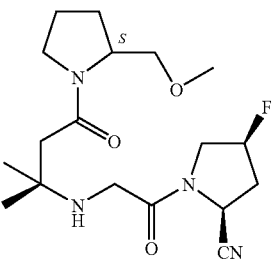
20
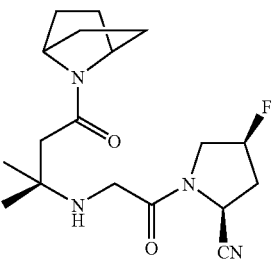
21
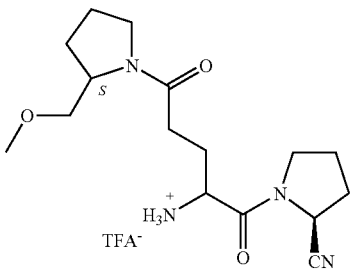
22
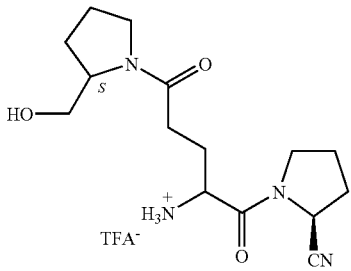
23
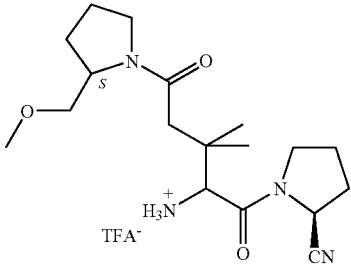
24
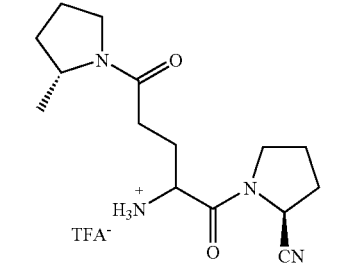

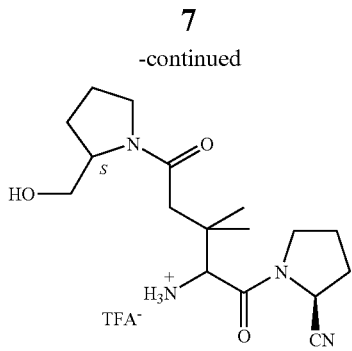

The term "alkyl" herein refers to a straight or branched hydrocarbon, containing 1-10 carbon atoms. Examples of alkyl groups include, but are not limited to, methyl, ethyl, n-propyl, i-propyl, n-butyl, i-butyl, and t-butyl. The term "alkoxy" refers to an —O-alkyl. The term "alkoxyalkyl" refers to an alkyl group substituted with one or more alkoxy groups. The term "haloalkyl" refers to an alkyl group substituted with one or more halo groups. The term "hydroxyalkyl" refers to an alkyl group substituted with one or more hydroxy groups.

The term "aryl" refers to a 6-carbon monocyclic, 10-carbon bicyclic, 14-carbon tricyclic aromatic ring system wherein each ring may have 1 to 4 substituents. Examples of aryl groups include, but are not limited to, phenyl, naphthyl, and anthracenyl. The term "aryloxy" refers to an —O-aryl. The term "aralkyl" refers to an alkyl group substituted with an aryl group.

The term "cyclyl" refers to a saturated and partially unsaturated cyclic hydrocarbon group having 3 to 12 carbons. Examples of cyclyl groups include, but are not limited to, cyclopropyl, cyclobutyl, cyclopentyl, cyclopentenyl, cyclohexyl, cyclohexenyl, cycloheptyl, and cyclooctyl.

The term "heteroaryl" refers to an aromatic 5-8 membered monocyclic, 8-12 membered bicyclic, or 11-14 membered tricyclic ring system having one or more heteroatoms (such as O, N, or S). Examples of heteroaryl groups include pyridyl, furyl, imidazolyl, benzimidazolyl, pyrimidinyl, thienyl, quinolinyl, indolyl, and thiazolyl. The term "heteroaralkyl" refers to an alkyl group substituted with a heteroaryl group.

The term "heterocyclyl" refers to a nonaromatic 5-8 membered monocyclic, 8-12 membered bicyclic, or 11-14 membered tricyclic ring system having one or more heteroatoms (such as O, N, or S). Examples of heterocyclyl groups include, but are not limited to, piperazinyl, pyrrolidinyl, dioxanyl, morpholinyl, and tetrahydrofuranyl.

Alkyl, cyclyl, heterocyclyl, aryl, heteroaryl, aralkyl, heteroaralkyl, alkoxy, and aryloxy mentioned herein include both substituted and unsubstituted moieties. Examples of substituents include, but are not limited to, halo, hydroxyl, amino, cyano, nitro, mercapto, alkoxycarbonyl, amido, carboxy, alkanesulfonyl, alkylcarbonyl, carbamido, carbamyl, carboxyl, thioureido, thiocyanato, sulfonamido, alkyl, alkenyl, alkynyl, alkyloxy, aryl, heteroaryl, cyclyl, heterocyclyl, in which alkyl, alkenyl, alkynyl, alkyloxy, aryl, heteroaryl cyclyl, and heterocyclyl may further substituted.

The monocyclic ring mentioned herein is either substituted or unsubstituted, but cannot be fused with another aromatic or non-aromatic ring.

The pyrrolidine compounds described above include their pharmaceutically acceptable salts and prodrugs, if applicable. Such a salt can be formed between a positively charged ionic group in a pyrrolidine compound (e.g., ammonium) and a negatively charged counterion (e.g., trifluoroacetate). Likewise, a negatively charged ionic group in a pyrrolidine compound (e.g., carboxylate) can also form a salt with a positively charged counterion (e.g., sodium, potassium, calcium, or magnesium). The pyrrolidine compounds may contain a non-aromatic double bond and one or more asymmetric centers. Thus, they can occur as racemic mixtures, single enantiomers, individual diastereomers, diastereomeric mixtures, and cis- or trans-isomeric forms. All such isomeric forms are contemplated.

The pyrrolidine compounds described above can be used to inhibit DPP-IV. Accordingly, another aspect of this invention relates to a method of inhibiting DPP-IV with one or more of the pyrrolidine compounds. As inhibition of DPP-IV results in reduced blood glucose levels and enhanced insulin secretion, the compounds of this invention can be also used to treat Type II diabetes. Thus, this invention further covers a method of treating Type II diabetes by administering to a subject in need of the treatment an effective amount of one or more of the pyrrolidine compounds.

Also within the scope of this invention is a pharmaceutical composition containing one or more of the above-described pyrrolidine compounds, as well as use of the composition for treatment of Type II diabetes and for manufacture of a medicament for the just-mentioned treatment.

The details of many embodiments of the invention are set forth in the detailed description and the claims below. Other features, objects, and advantages of the invention will be apparent from the detailed description and the claims.

DETAILED DESCRIPTION

The pyrrolidine compounds of this invention can be synthesized by methods well known in the art. Exemplary methods for synthesizing these compounds are shown in Schemes 1-3 below.

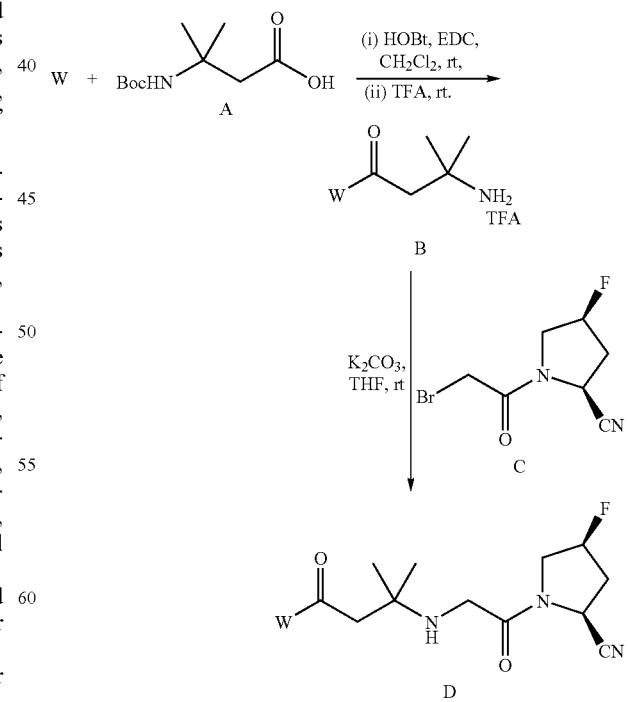

Scheme 1 illustrates a synthetic route to compounds of formula (I). Starting material (A) is a N-protected β-amino acid. It reacts with amine (W) in the presence of a coupling agent, e.g., N-(3-dimethylaminopropyl)-N-ethylcarbodiimide (EDC), followed by deprotection, to provide amide (B), which has a free amino group. The amide is then coupled with pyrrolidine (C) to form the desired compound (D). N-protected β-amino acid (A) and pyrrolidine (C) can be prepared by known methods. See, e.g., *J. Med. Chem.* 2006, 49, 373; *J. Med. Chem.* 1988, 31, 92; *J. Med. Chem.* 2002, 45, 2362; and *Bioorg. Med. Chem.* 2004, 12, 6053.

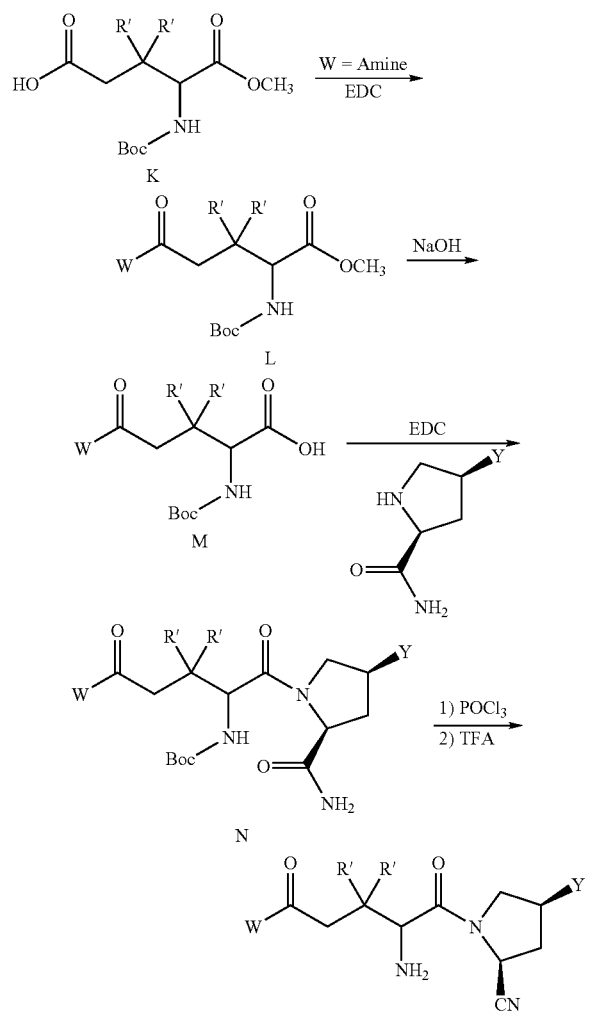

R = CH$_3$
R' = H or CH$_3$
Y = H or F

Scheme 2 illustrates a synthetic route to compounds of formula (II). In this scheme, the starting compound is amino-substituted dicarboxylic acid (K), in which an amino group and one of two carboxy groups are protected. Compound (K) is coupled with an amine to give compound L, which is hydrolyzed to afford acid (M). Acid (M) is coupled with L-prolinamide to give compound (N). Compound (N) is dehydrated followed by removal of the amino-protecting group to give the desired product (O). Some compounds used in the above synthesis can be prepared by methods well known in the art. See, e.g., *Bioorg. Med. Chem.* 2004, 12, 6053.

The above schemes are provided only for illustrative purposes. A skilled person in the art would be able to synthesize all the pyrrolidine compounds of this invention via a route shown in the schemes with or without modifications. Synthetic chemistry transformations and protecting group methodologies (protection and deprotection) useful in synthesizing applicable pyrrolidine compounds are known in the art and include, for example, those described in R. Larock, *Comprehensive Organic Transformations*, VCH Publishers (1989); T. W. Greene and P. G. M. Wuts, *Protective Groups in Organic Synthesis*, 3$^{rd}$ Ed., John Wiley and Sons (1999); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995) and subsequent editions thereof.

Pyrrolidine compounds thus obtained can be further purified by column chromatography, high performance liquid chromatography, or crystallization.

This invention covers a method for inhibiting DPP-IV by contacting it with an effective amount of one or more of the pyrrolidine compounds described above. This invention also covers a method for treating Type II diabetes by administering to a subject in need thereof an effective amount of one or more of the pyrrolidine compounds described above. The term "treating" refers to application or administration of the pyrrolidine compound to a subject, who has Type II diabetes, a symptom of Type II diabetes, or a predisposition toward Type II diabetes, with the purpose to cure, heal, alleviate, relieve, alter, remedy, ameliorate, improve, or affect the disease, the symptom, or the predisposition. "An effective amount" refers to the amount of the pyrrolidine compound which is required to confer the desired effect on the subject. Effective amounts vary, as recognized by those skilled in the art, depending on route of administration, excipient usage, and the possibility of co-usage with other therapeutic treatments such as use of other active agents.

To practice the treatment method of the present invention, a composition having one or more of the pyrrolidine compounds describe above can be administered parenterally, orally, nasally, rectally, topically, or buccally. The term "parenteral" as used herein refers to subcutaneous, intracutaneous, intravenous, intramuscular, intraarticular, intraarterial, intrasynovial, intrasternal, intrathecal, intralesional, or intracranial injection, as well as any suitable infusion technique.

A sterile injectable composition can be a solution or suspension in a non-toxic parenterally acceptable diluent or solvent, such as a solution in 1,3-butanediol. Among the acceptable vehicles and solvents that can be employed are mannitol and water. In addition, fixed oils are conventionally employed as a solvent or suspending medium (e.g., synthetic mono- or diglycerides). Fatty acids, such as oleic acid and its glyceride derivatives, are useful in the preparation of injectables, as are natural pharmaceutically acceptable oils, such as olive oil or castor oil, especially in their polyoxyethylated versions. These oil solutions or suspensions can also contain a long chain alcohol diluent or dispersant, carboxymethyl cellulose, or similar dispersing agents. Other commonly used surfactants such as Tweens or Spans or other similar emulsifying agents or bioavailability enhancers which are commonly used in the manufacture of pharmaceutically acceptable solid, liquid, or other dosage forms can also be used for the purpose of formulation.

A composition for oral administration can be any orally acceptable dosage form including capsules, tablets, emulsions and aqueous suspensions, dispersions, and solutions. In the case of tablets, commonly used carriers include lactose and corn starch. Lubricating agents, such as magnesium stearate, are also typically added. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added.

A nasal aerosol or inhalation composition can be prepared according to techniques well known in the art of pharmaceutical formulation. For example, such a composition can be prepared as a solution in saline, employing benzyl alcohol or other suitable preservatives, absorption promoters to enhance bioavailability, fluorocarbons, and/or other solubilizing or dispersing agents known in the art. A composition having an active pyrrolidine compounds can also be administered in the form of suppositories for rectal administration.

The carrier in the pharmaceutical composition must be "acceptable" in the sense that it is compatible with the active ingredient of the composition (and preferably, capable of stabilizing the active ingredient) and not deleterious to the subject to be treated. One or more solubilizing agents can be utilized as pharmaceutical excipients for delivery of an active pyrrolidine compound. Examples of other carriers include colloidal silicon oxide, magnesium stearate, cellulose, sodium lauryl sulfate, and D&C Yellow # 10.

Pyrrolidine compounds of this invention can be used alone or together with another diabetes drug in treating Type II diabetes. Examples of diabetes drugs include, but are not limited to, an insulin secretagogue (sulphonylureas or meglitinides), an insulin sensitizer (thiazolidinediones), a biguanide, or an α-glucosidase inhibitor.

The pyrrolidine compounds of this invention can be preliminarily screened by an in vitro assay for one or more of their desired activities, e.g., inhibiting DPP-IV. Compounds that demonstrate high activities in the preliminary screening can further be screened for their efficacy by in vivo assays. For example, a test compound can administered to an animal (e.g., a mouse model) having type II diabetes and its therapeutic effects are then accessed. Based on the results, an appropriate dosage range and administration route can also be determined.

The specific examples below are to be construed as merely illustrative, and not limitative of the remainder of the disclosure in any way whatsoever. Without further elaboration, it is believed that one skilled in the art can, based on the description herein, utilize the present invention to its fullest extent. All of the publications cited herein are hereby incorporated by reference in their entirety.

Example 1

Synthesis of (2S,4S)-1-[2-(1,1-dimethyl-3-oxo-3-pyrrolidin-1-yl-propylamino)-acetyl]-4-fluoro-pyrrolidine-2-carbonitrile (compound 1)

(1) Preparation of 3-amino-3-methyl-1-pyrrolidin-1-yl-butan-1-one, trifluoroacetic acid To a mixture of 3-(tert-butoxycarbonylamino)-3-methylbutanoic acid (0.87 g, 4 mmol), pyrrolidine (0.28 g, 4 mmol), and 1-hydroxybenzotriazole hydrate (HOBt hydrate, 0.54 g, 4 mmol) in $CH_2Cl_2$ (10 mL) was added N-ethyl-N'-(3-dimethylaminopropyl)carbodiimide hydrochloride (EDC, 0.77 g, 4 mmol). The reaction mixture was stirred at ambient temperature for 12 h, diluted with $CH_2Cl_2$ (40 mL), and washed with saturated aqueous sodium bicarbonate (20 mL), 0.5 N aqueous citric acid (20 mL) and brine (20 mL). The organic layer was separated, dried over magnesium sulfate, filtered, and concentrated under reduced pressure to yield a crude viscous oil. The crude oil was purified by flash chromatography (silica gel, 40% ethyl acetate/hexanes) to give N-Boc-protected amine (1.03 g) as a colorless oil.

A solution of the above amine in trifluoroacetic acid (TFA, 2 mL) was stirred at room temperature for 10 min and concentrated in vacuo to afford 3-amino-3-methyl-1-pyrrolidin-1-yl-butan-1-one trifluoroacetic acid (1.08 g, 95% overall yield) as a colorless oil which was used in the next step without further purification.

(2) Preparation of (2S,4S)-1-[2-(1,1-dimethyl-3-oxo-3-pyrrolidin-1-yl-propylamino)-acetyl]-4-fluoropyrrolidine-2-carbonitrile (Compound 1)

To a stirred solution of 3-amino-3-methyl-1-pyrrolidin-1-yl-butan-1-one trifluoroacetic acid (0.28 g, 1 mmol) in anhydrous THF (5 mL) was added potassium carbonate (0.55 g, 4 mmol). After stirred at room temperature for 1 h, the mixture was filtered through a Celite pad, and rinsed with ethyl acetate (5 mL). To the above filtrate was added (2S,4S)-1-(2-bromoacetyl)-4-fluoropyrrolidine-2-carbonitrile (0.12 g, 0.5 mmol) and the reaction mixture was stirred at room temperature under nitrogen for 12 h. Most of solvent was removed under reduced pressure and the residue was partitioned between $CH_2Cl_2$ (20 mL) and $H_2O$ (5 mL). The aqueous layer was further extracted with $CH_2Cl_2$ (10 mL). The combined organic layers were dried over magnesium sulfate, filtered, and concentrated under reduced pressure to yield a crude viscous oil. The crude oil was purified by chromatography (silica gel, 4 to 10% $CH_3OH/CH_2Cl_2$ gradient) to give compound 1 (0.12 g, 74% overall yield) as a white solid.

$^1$H NMR (CDCl$_3$, 300 MHz, δ): (2/1 mixture of trans/cis amide rotomers) 5.53 (d, J=9.0 Hz, ⅓H), 5.49 (t, J=3.3 Hz, ⅓H), 5.40 (t, J=3.3 Hz, ⅙H), 5.32 (t, J=3.3 Hz, ⅓H), 5.22 (t, J=3.3 Hz, ⅙H), 4.95 (d, J=9.0 Hz, ⅔H), 4.04-3.52 (m, 2 H), 3.48-3.39 (m, 6H), 2.70 (t, J=15.9 Hz, ⅓H), 2.62 (t, J=15.9 Hz, ⅔H), 2.44-2.26 (m, 3H, overlapped singlet at 2.39), 1.98-1.79 (m, 4H), 1.22 (s, 6H);

MS (ES) m/z calcd. for $C_{16}H_{25}FN_4O_2$: 324.39; found: 325.2 (M+H), 347.2 (M+Na).

Example 2

Synthesis of (2S,4S)-1-[2-(1,1-dimethyl-3-morpholin-4-yl-3-oxo-propylamino)-acetyl]-4-fluoro-pyrrolidine-2-carbonitrile (compound 2)

Compound 2 was prepared in a similar manner to that described in Example 1.

$^1$H NMR (CDCl$_3$, 300 MHz, δ): (2/1 mixture of trans/cis amide rotomers) 5.50 (t, J=3.3 Hz, ⅓H), 5.42 (t, J=3.3 Hz, ⅙H), 5.38 (d, J=9.0 Hz, ⅓H), 5.32 (t, J=3.3 Hz, ⅓H), 5.23 (t, J=3.3 Hz, ⅙H), 4.94 (d, J=9.0 Hz, ⅔H), 4.12-3.35 (m, 12H, overlapped singlet at 3.41), 2.70 (t, J=15.6 Hz, ⅓H), 2.65 (t, J=15.6 Hz, ⅔H), 2.50-2.18 (m, 3H), 1.20 (s, 6H);

MS (ES$^+$) m/z calcd. for $C_{16}H_{25}FN_4O_3$: 340.39; found: 341.2 (M+H), 363.2 (M+Na).

Example 3

Synthesis of 3-[2-((2S,4S)-2-cyano-4-fluoro-pyrrolidin-1-yl)-2-oxo-ethylamino]-3-methyl-N-pyridin-3-yl-butyramide (compound 3)

Compound 3 was prepared in a similar manner to that described in Example 1.

$^1$H NMR (CDCl$_3$, 300 MHz, δ): (3/1 mixture of trans/cis amide rotomers) 11.12 (brs, ¾H), 11.01 (brs, ¼H), 8.66-8.63 (m, 1H), 8.28 (d, J=4.5 Hz, 1H), 8.22-8.14 (m, 1H), 7.26-7.21 (m, 1H), 5.53 (t, J=3.3 Hz, ⅜H), 5.46 (t, J=3.3 Hz, ⅛H), 5.36

(t, J=3.3 Hz, ⅜H), 5.29 (t, J=3.3 Hz, ⅛H), 4.98 (d, J=9.3 Hz, ¾H), 4.80 (d, J=9.3 Hz, ¼H), 3.97-3.61 (m, 2H), 3.46 (q like, J=16.8 Hz, 2H), 2.79 (t, J=15.3 Hz, ¼H), 2.71 (t, J=15.3 Hz, ¾H), 2.50-2.39 (m, 3H, overlapped 2 singlet at 2.45, 2.44), 1.26 (s, 3H), 1.24 (s, 3H);

MS (ES$^-$) m/z calcd. for $C_{17}H_{22}FN_5O_2$: 347.39; found: 348.2 (M+H), 370.2 (M+Na).

Example 4

Synthesis of (2S,4S)-4-fluoro-1-{2-[3-((R)-3-hydroxy-pyrrolidin-1-yl)-1,1-dimethyl-3-oxo-propylamino]-acetyl}-pyrrolidine-2-carbonitrile (compound 4)

Compound 4 was prepared in a similar manner to that described in Example 1.

$^1$H NMR (CDCl$_3$, 300 MHz, δ): (2/1 mixture of trans/cis amide rotomers) 5.50 (t, J=3.3 Hz, ⅓H), 5.40 (t, J=3.3 Hz, ⅙H), 5.38 (d, J=9.0 Hz, ⅓H), 5.32 (t, J=3.3 Hz, ⅓H), 5.23 (t, J=3.3 Hz, ⅙H), 4.94 (d, J=9.0 Hz, ⅔H), 4.47-4.21 (m, 1 H), 3.99-3.22 (m, 8H), 2.84 (brs, OH), 2.69 (t, J=15.3 Hz, ⅓H), 2.61 (t, J=15.3 Hz, ⅔H), 2.50-2.15 (m, 3H), 2.04-1.89 (m, 2H), 1.21 (s, 3H), 1.18 (s, 3H);

MS (ES$^-$) m/z calcd. for $C_{16}H_{25}FN_4O_3$: 340.39; found: 341.2 (M+H), 363.2 (M+Na).

Example 5

Synthesis of (2S,4S)-4-fluoro-1-(2-(2-methyl-4-(4-(methylsulfonyl)piperazin-1-yl)-4-oxobutan-2-ylamino)acetyl)pyrrolidine-2-carbonitrile (compound 5)

Compound 5 was prepared in a similar manner to that described in Example 1.

Example 6

Synthesis of (2S,4S)-4-fluoro-1-(2-(4-((R)-3-fluoro-pyrrolidin-1-yl)-2-methyl-4-oxobutan-2-ylamino)acetyl)pyrrolidine-2-carbonitrile (compound 6)

Compound 6 was prepared in a similar manner to that described in Example 1.

$^1$H NMR (CDCl$_3$, 300 MHz, δ): (3/1 mixture of trans/cis amide rotomers) 5.50 (t, J=3.0 Hz, ⅜H), 5.41 (t, J=3.0 Hz, ⅛H), 5.3 (t, J=3.0 Hz, ⅜H), 5.25 (t, J=3.0 Hz, ⅛H), 5.23 (d, J=9.3 Hz, ¼H), 4.92 (d, J=9.3 Hz, ¾H), 4.00-3.40 (m, 8H, overlapped singlet at 3.46), 3.31-3.20 (m, 4H), 2.80 (s, ¾H), 2.78 (s, ¾H), 2.69 (t, J=15.6 Hz, ¼H), 2.64 (t, J=15.6 Hz, ¾H), 2.54-2.23 (m, 3H, overlapped singlet at 2.51), 1.24 (s, 6H);

MS (ES$^-$) m/z calcd. for $C_{17}H_{28}FN_5O_4S$: 417.50; found: 418.2 (M+H), 440.1 (M+Na).

Example 7

Synthesis of 3-[2-((2S,4S)-2-cyano-4-fluoro-pyrrolidin-1-yl)-2-oxo-ethylamino]-3-methyl-N-(5-methyl-thiazol-2-yl)-butyramide (compound 7)

Compound 7 was prepared in a similar manner to that described in Example 1.

$^1$H NMR (CDCl$_3$, 300 MHz, δ): (3/1 mixture of trans/cis amide rotomers) 6.48 (s, 1H), 5.53 (t, J=3.3 Hz, ⅜H), 5.45 (t, J=3.3 Hz, ⅛H), 5.36 (t, J=3.3 Hz, ⅜H), 5.32 (t, J=3.3 Hz, ⅛H), 4.89 (d, J=9.0 Hz, ¾H), 4.87 (d, J=9.0 Hz, ¼H), 4.12-3.63 (m, 2H), 3.52-3.39 (m, 2H), 2.75 (t, J=15.6 Hz, ¼H), 2.70 (t, J=15.6 Hz, ¾H), 2.60-2.26 (m, 6H, overlapped doublet at 2.51, J=2.4 Hz and a singlet at 2.31), 1.25 (s, 3H), 1.22 (s, 3H);

MS (ES$^-$) m/z calcd. for $C_{16}H_{22}FN_5O_2S$: 367.44; found: 368.1 (M+H), 390.1 (M+Na).

Example 8

Synthesis of 3-[2-((2S,4S)-2-cyano-4-fluoro-pyrrolidin-1-yl)-2-oxo-ethylamino]-N-(6-methoxy-pyridin-3-yl)-3-methyl-butyramide (compound 8)

Compound 8 was prepared in a similar manner to that described in Example 1.

$^1$H NMR (CDCl$_3$, 300 MHz, δ): (3/1 mixture of trans/cis amide rotomers) 10.76 (brs, ¾H), 10.59 (brs, ¼H), 8.29-8.26 (m, 1H), 7.96 (dd, J=9.0, 3.0 Hz, 1H), 6.70 (d, J=9.0 Hz, 1H), 5.54 (t, J=3.6 Hz, ⅜H), 5.46 (t, J=3.6 Hz, ⅛H), 5.36 (t, J=3.6 Hz, ⅜H), 5.29 (t, J=3.6 Hz, ⅛H), 4.98 (d, J=9.0 Hz, ¾H), 4.80 (d, J=9.0 Hz, ¼H), 4.13-3.55 (m, 5H, overlapped singlet at 3.89), 3.45 (q like, J=16.2 Hz, 2H), 2.79 (t, J=15.3 Hz, ¼H), 2.71 (t, J=15.3 Hz, ¾H), 2.49-2.23 (m, 3H, overlapped 2 singlet at 2.44, 2.42), 1.26 (s, 3H), 1.24 (s, 3H);

MS (ES$^+$) m/z calcd. for $C_{18}H_{24}FN_5O_3$: 377.41; found: 378.2 (M+H), 400.1 (M+Na).

Example 9

Synthesis of (2S,4S)-1-{2-[3-(3,6-dihydro-2H-pyridin-1-yl)-1,1-dimehtyl-3-oxo-propylamino]-acetyl}-4-fluoro-pyrrolidine-2-carbonitrile (compound 9)

Compound 9 was prepared in a similar manner to that described in Example 1.

$^1$H NMR (CDCl$_3$, 300 MHz, δ): (2/1 mixture of trans/cis amide rotomers) 5.89-5.77 (m, 1H), 5.69-5.60 (m, 1H), 5.49 (t, J=3.3 Hz, ⅓H), 5.46 (d, J=9.3 Hz, ⅓H), 5.40 (t, J=3.3 Hz, ⅙H), 5.31 (t, J=3.3 Hz, ⅓H), 5.22 (t, J=3.3 Hz, ⅙H), 4.92 (d, J=9.3 Hz, ⅔H), 4.02-3.39 (m, 8H), 2.67 (t, J=15.3 Hz, ⅓H), 2.61 (t, J=15.3 Hz, ⅔H), 2.48-2.12 (m, 5H), 1.19 (s, 3H), 1.18 (s, 3H);

MS (ES$^-$) m/z calcd. for $C_{17}H_{25}FN_4O_2$: 336.40; found: 337.2 (M+H), 359.2 (M+Na).

Example 10

Synthesis of (2S,4S)-1-[2-(1,1-dimethyl-3-oxo-3-thiazolidin-3-yl-propylamino)-acetyl]-4-fluoro-pyrrolidine-2-carbonitrile (compound 10)

Compound 10 was prepared in a similar manner to that described in Example 1.

$^1$H NMR (CDCl$_3$, 300 MHz, δ): (2/1 mixture of trans/cis amide rotomers) 5.52 (t, J=3.3 Hz, ⅓H), 5.43 (t, J=3.3 Hz, ⅙H), 5.36 (t, J=3.3 Hz, ⅓H), 5.33 (d, J=9.0 Hz, ⅓H), 5.25 (t, J=3.3 Hz, ⅙H), 4.96 (d, J=9.0 Hz, ⅔H), 4.57 (s, 1H), 4.51 (s, 1H), 4.02-3.04 (m, 6H, overlapped singlet at 3.43), 3.10 (t, J=6.3 Hz, 1H), 3.00 (t, J=6.3 Hz, 1H), 2.75 (t, J=15.6 Hz, ⅓H), 2.64 (t, J=15.6 Hz, ⅔H), 2.51-2.24 (m, 3H, overlapped 2 singlet at 2.47, 2.46), 1.23 (s, 6H);

MS (ES$^-$) m/z calcd. for $C_{15}H_{23}FN_4O_2S$: 342.43; found: 343.1 (M+H), 365.1 (M+Na).

Example 11

Synthesis of (2S,4S)-1-[2-(1,1-dimethyl-3-oxo-3-piperidin-1-yl-propylamino)-acetyl]-4-fluoro-pyrrolidine-2-carbonitrile (compound 11)

Compound 11 was prepared in a similar manner to that described in Example 1.

¹H NMR (CDCl₃, 300 MHz, δ): (2/1 mixture of trans/cis amide rotomers) 5.48 (t, J=3.3 Hz, ⅓H), 5.45 (d, J=9.3 Hz, ⅓H), 5.39 (t, J=3.3 Hz, ⅙H), 5.30 (t, J=3.3 Hz, ⅓H), 5.22 (t, J=3.3 Hz, ⅙H), 4.93 (d, J=9.3 Hz, ⅔H), 4.00-3.35 (m, 8H), 2.67 (t, J=15.6 Hz, ⅓H), 2.60 (t, J=15.6 Hz, ⅔H), 2.50-2.20 (m, 3H, overlapped single at 2.41), 1.64-1.44 (m, 6H), 1.18 (s, 6H);
MS (ES⁻) m/z calcd. for $C_{17}H_{27}FN_4O_2$: 338.42; found: 339.2 (M+H), 361.2 (M+Na).

Example 12

Synthesis of 4-{3-[2-((2S,4S)-2-cyano-4-fluoro-pyrrolidin-1-yl)-2-oxo-ethylamino]-3-methyl-butyryl}-piperazine-1-carboxylic acid ethyl ester (compound 12)

Compound 12 was prepared in a similar manner to that described in Example 1.
¹H NMR (CDCl₃, 300 MHz, δ): (2/1 mixture of trans/cis amide rotomers) 5.51 (t, J=3.3 Hz, ⅓H), 5.42 (t, J=3.3 Hz, ⅙H), 5.36 (d, J=9.0 Hz, ⅓H), 5.34 (t, J=3.3 Hz, ⅓H), 5.25 (t, J=3.3 Hz, ⅙H), 4.96 (d, J=9.0 Hz, ⅔H), 4.16 (q, J=6.9 Hz, 2H), 4.19-3.38 (m, 12H), 2.72 (t, J=15.3 Hz, ⅓H), 2.65 (t, J=15.3 Hz, ⅔H), 2.53-2.22 (m, 3H, overlapped 2 singlet at 2.46, 2.43), 1.27 (t, J=6.9 Hz, 3H), 1.22 (s, 6H).
MS (ES⁻) m/z calcd. for $C_{19}H_{30}FN_5O_4$: 411.47; found: 412.2 (M+H), 434.2 (M+Na).

Example 13

Synthesis of 3-[2-((2S,4S)-2-cyano-4-fluoro-pyrrolidin-1-yl)-2-oxo-ethylamino]-N-cyclopentyl-3-methyl-butyramide (compound 13)

Compound 13 was prepared in a similar manner to that described in Example 1.
¹H NMR (CDCl₃, 300 MHz, δ): (4/1 mixture of trans/cis amide rotomers) 7.94 (d, J=7.2 Hz, ⅘H), 7.59 (d, J=7.2 Hz, ⅕H), 5.51 (t, J=3.3 Hz, ⅖H), 5.4 (t, J=3.3 Hz, 1/10H), 5.34 (t, J=3.3 Hz, ⅖H), 5.25 (t, J=3.3 Hz, 1/10H), 5.02 (d, J=9.0 Hz, ⅕H), 4.92 (d, J=9.0 Hz, ⅘H), 4.20-4.07 (m, 1H), 4.03-3.27 (m, 4H), 2.73 (t, J=15.6 Hz, ⅕H), 2.65 (t, J=15.6 Hz, ⅘H), 2.44-2.10 (m, 3H), 1.91-1.82 (m, 2H), 1.68-1.48 (m, 4H), 1.43-1.31 (m, 2H), 1.15 (s, 6H).
MS (ES⁻) m/z calcd. for $C_{17}H_{27}FN_4O_2$: 338.42; found: 339.4 (M+H), 361.4 (M+Na).

Example 14

Synthesis of (2S,4S)-4-fluoro-1-{2-[3-((S)-2-hydroxymethyl-pyrrolidin-1-yl)-1,1-dimethyl-3-oxo-propylamino]-acetyl}-pyrrolidine-2-carbonitrile (compound 14)

Compound 14 was prepared in a similar manner to that described in Example 1.
¹H NMR (CDCl₃, 300 MHz, δ): (2/1 mixture of trans/cis amide rotomers) 5.50 (t, J=3.3 Hz, ⅓H), 5.41 (t, J=3.3 Hz, ⅙H), 5.37 (d, J=9.3 Hz, ⅓H), 5.32 (t, J=3.3 Hz, ⅓H), 5.22 (t, J=3.3 Hz, ⅙H), 4.95 (d, J=9.0 Hz, ⅔H), 4.26-4.19 (m, 1H), 4.03-3.37 (m, 8H, overlapped singlet at 3.43), 2.70 (t, J=15.6 Hz, ⅓H), 2.63 (t, J=15.6 Hz, ⅔H), 2.55 (brs, OH), 2.52-2.21 (m, 3H, overlapped singlet at 2.42), 2.07-1.79 (m, 3H), 1.69-1.57 (m, 1H), 1.22 (s, 6H);
MS (ES⁻) m/z calcd. for $C_{17}H_{27}FN_4O_3$: 354.42; found: 355.2 (M+H), 377.2 (M+Na).

Example 15

Synthesis of (2S,4S)-1-{2-[1,1-dimethyl-3-((R)-2-methyl-pyrrolidin-1-yl)-3-oxo-propylamino]-acetyl}-4-fluoro-pyrrolidine-2-carbonitrile (compound 15)

Compound 15 was prepared in a similar manner to that described in Example 1.
¹H NMR (CDCl₃, 300 MHz, δ): (2/1 mixture of trans/cis amide rotomers) 5.52-5.47 (m, ⅔H), 5.39 (t, J=3.3 Hz, ⅙H), 5.31 (t, J=3.3 Hz, ⅓H), 5.22 (t, J=3.3 Hz, ⅙H), 4.92 (d, J=9.3 Hz, ⅔H), 4.19-3.31 (m, 6H, overlapped singlet at 3.39), 2.78-2.19 (m, 5H), 2.02-1.83 (m, 3H), 1.68-1.49 (m, 1H), 1.19-1.12 (m, 9H);
MS (ES) m/z calcd. for $C_{17}H_{27}FN_4O_2$: 338.42; found: 339.4 (M+H), 361.4 (M+Na).

Example 16

Synthesis of (2S,4S)-1-{2-[3-(1,3-dihydro-isoindol-2-yl)-1,1-dimethyl-3-oxo-propylamino]-acetyl}-4-fluoro-pyrrolidine-2-carbonitrile (compound 16)

Compound 16 was prepared in a similar manner to that described in Example 1.
¹H NMR (CDCl₃, 300 MHz, δ): (3/1 mixture of trans/cis amide rotomers) 7.30-7.16 (m, 4H), 5.52 (d, J=9.3 Hz, ¼H), 5.50 (t, J=3.3 Hz, ⅜H), 5.40 (t, J=3.3 Hz, ⅛H), 5.31 (t, J=3.3 Hz, ⅜H), 5.23 (t, J=3.3 Hz, ⅛H), 4.94 (d, J=9. Hz, ¾H), 4.83 (s, 2H), 4.78 (s, 2H), 4.15-3.35 (m, 4H, overlapped singlet at 3.45), 2.70 (t, J=15.3 Hz, ¼H), 2.64 (t, J=15.3 Hz, ¾H), 2.59-2.18 (m, 3H), 1.22 (s, 6H);
MS (ES⁻) m/z calcd. for $C_{20}H_{25}FN_4O_2$: 372.44; found: 373.2 (M+H), 395.2 (M+Na).

Examples 17-20

Synthesis of Compounds 17-20

Compounds 17-20 were prepared in similar manners to that described in Example 1.

Example 21

Synthesis of (2S)-1-[2-amino-5-((S)-2-methoxymethyl-pyrrolidin-1-yl)-5-oxo-pentanoyl]-pyrrolidine-2-carbonitrile trifluoroacetic acid (compound 21)

(1) Preparation of 2-tert-butoxycarbonylamino-5-((S)-2-methoxymethyl-pyrrolidin-1-yl)-5-oxo-pentanoic acid methyl ester To a mixture of 4-(tert-butoxycarbonylamino)-5-methoxy-5-oxopentanoic acid (1.05 g, 4 mmol), (S)-2-(methoxymethyl)-pyrrolidine (0.46 g, 4 mmol), and 1-hydroxybenzotriazole hydrate (HOBt hydrate, 0.54 g, 4 mmol) in $CH_2Cl_2$ (10 mL) was added EDC (0.77 g, 4 mmol). The reaction mixture was stirred at ambient temperature for 12 h, diluted with $CH_2Cl_2$ (40 mL), washed sequentially with saturated aqueous sodium bicarbonate (20 mL), 0.5 N aqueous citric acid (20 mL) and brine (20 mL), dried over magnesium sulfate, filtered, and concentrated under reduced pressure to yield a crude viscous oil. The crude oil was purified by flash chromatography (silica gel, 50% ethyl acetate/hexanes) to give the title compound (1.36 g, 95%) as a colorless oil.

(2) Preparation of 2-tert-butoxycarbonylamino-5-((S)-2-methoxymethyl-pyrrolidin-1-yl)-5-oxo-pentanoic acid To a stirred solution of 2-tert-butoxycarbonylamino-5-((S)-2-methoxymethyl-pyrrolidin-1-yl)-5-oxo-pentanoic acid methyl ester (0.72 g, 2 mmol) in $CH_3OH$ (20 mL) was added 2 N aqueous sodium hydroxide (20 mL). After stirred at room temperature for 12 h, the mixture was acidified by the addition of 6 N aqueous hydrochloric acid at 0° C. to pH=4. Most of methanol was removed under reduced pressure and the residue was partitioned between $CH_2Cl_2$ (20 mL) and $H_2O$ (20 mL). The aqueous layer was further extracted with $CH_2Cl_2$ (20 mL). The combined organic layers were dried over magnesium sulfate, filtered, and concentrated under reduced pressure to yield the title compound (0.54 g, 79%) as a foamy solid which was used in the next step without further purification.

(3) Preparation of tert-butyl 1-((S)-2-carbamoylpyrrolidin-1-yl)-5-((S)-2-(methoxymethyl)pyrrolidin-1-yl)-1,5-dioxopentan-2-ylcarbamate To a mixture of 2-tert-butoxycarbonylamino-5-((S)-2-methoxymethyl-pyrrolidin-1-yl)-5-oxo-pentanoic acid (0.34 g, 1 mmol), L-prolinamide (0.11 g, 1 mmol), and HOBt hydrate (0.14 g, 1 mmol) in $CH_2Cl_2$ (5 mL) was added EDC (0.19 g, 1 mmol). The reaction mixture was stirred at ambient temperature for 12 h, diluted with $CH_2Cl_2$ (20 mL), washed sequentially with saturated aqueous sodium bicarbonate (10 mL), 0.5 N aqueous citric acid (10 mL) and brine (10 mL), dried over magnesium sulfate, filtered, and concentrated under reduced pressure to yield a crude a viscous oil. The crude oil was purified by flash chromatography (silica gel, 2 to 8% $CH_3OH/CH_2Cl_2$ gradient) to give the title compound (0.36 g, 81%) as a foamy solid.

(4) Preparation of (2S)-1-[2-amino-5-((S)-2-methoxymethyl-pyrrolidin-1-yl)-5-oxo-pentanoyl]-pyrrolidine-2-carbonitrile trifluoroacetic acid (compound 21)

To a mixture of tert-butyl 1-((S)-2-carbamoylpyrrolidin-1-yl)-5-((S)-2-(methoxymethyl)pyrrolidin-1-yl)-1,5-dioxopentan-2-ylcarbamate (0.36 g, 0.8 mmol) and imidazole (0.68 g, 1 mmol) in pyridine (4 mL) at −20° C. was added phosphoryl chloride (0.32 g, 2.1 mmol). The slurry was stirred at −20° C. for 1 h, warmed to room temperature, and concentrated in vacuo. The residue was partitioned between $CH_2Cl_2$ (10 mL) and 0.5 N aqueous citric acid (10 mL). The aqueous layer was further extracted with $CH_2Cl_2$ (10 mL). The combined organic layers were dried over magnesium sulfate, filtered, and concentrated under reduced pressure to yield a pale yellow oil. The crude oil was purified by flash chromatography (silica gel, 50% ethyl acetate/dichloromethane) to give a colorless oil.

A solution of the above oil in trifluoroacetic acid (TFA, 1 mL) was stirred at room temperature for 10 min and concentrated in vacuo to afford compound 21 (0.27 g, 77%) as a foamy solid.

MS (ES$^-$) m/z calcd. for $C_{16}H_{26}N_4O_3$: 322.40; found: 323.6 (M+H), 345.6 (M+Na).

Example 22

Synthesis of (2S)-1-[2-amino-5-((S)-2-hydroxymethyl-pyrrolidin-1-yl)-5-oxo-pentanoyl]-pyrrolidine-2-carbonitrile trifluoroacetic acid (compound 22)

Compound 22 was prepared in a similar manner to that described in Example 21.

MS (ES$^-$) m/z calcd. for $C_{15}H_{24}N_4O_3$: 308.38; found: 309.1 (M+H), 331.1 (M+Na).

Example 23

Synthesis of (2S)-1-[2-amino-5-((S)-2-methoxymethyl-pyrrolidin-1-yl)-3,3-dimethyl-5-oxo-pentanoyl]-pyrrolidine-2-carbonitrile trifluoroacetic acid (compound 23)

Compound 23 was prepared in a similar manner to that described in Example 21.

MS (ES$^-$) m/z calcd. for $C_{18}H_{30}N_4O_3$: 350.46; found: 351.6 (M+H), 373.7 (M+Na).

Example 24

Synthesis of (2S)-1-[2-amino-5-((R)-2-methyl-pyrrolidin-1-yl)-5-oxo-pentanoyl]-pyrrolidine-2-carbonitrile trifluoroacetic acid (compound 24)

Compound 24 was prepared in a similar manner to that described in Example 21.

MS (ES$^-$) m/z calcd. for $C_{18}H_{30}N_4O_3$: 292.38; found: 293.6 (M+H), 315.6 (M+Na).

Example 25

Synthesis of (2S)-1-(2-amino-5-((S)-2-(hydroxymethyl)pyrrolidin-1-yl)-3,3-dimethyl-5-oxopentanoyl)pyrrolidine-2-carbonitrile trifluoroacetic acid (compound 25)

Compound 25 was prepared in a similar manner to that described in Example 21.

Example 26

DPP-IV was purified from both human serum and insect cells in a manner similar to that described in *Biochemistry*, 2006, 45: 7006-7012.

DPP-VIII was purified from baculovirus-infected sfa cells in a manner similar to that described in *J. Biol. Chem.* 2006, 28: 138653-138662.

The purity of DPP-IV or DPP-VIII was checked by SDS-PAGE, followed by commassie blue stain or silver stain. DPP-IV and DPP-VIII concentrations were measured by the Bradford method using BSA as the standard (*Anal. Biochem.* 1976, 72: 248-254.)

Compounds 1-24 were tested for their inhibitory effect on DPP-IV as follows: For each compound, 8 serial dilutions (final concentrations from 0.0046 to 10 μmol/l) were prepared and used. 40 μl of DPP-IV in Tris (40 mM, pH 8.3) was incubated with 10 μl of the test compound in Tris containing 1% DMSO at 37° C. incubator at room temperature for 10 min. 50 μl of Gly-Pro-7-amino-4-methylcoumarin (final concentration: 150 μM) was added to the solution and incubated at 37° C. for 1 h. Release of 7-amino-4-methylcoumarin was monitored continuously in a 96-well plate fluorometer (Victor$^2$ V) and data were recorded at the endpoint of the inhibition reaction. IC$_{50}$ values were calculated based on the results.

Similarly, compounds 1-24 were tested for their inhibitory effect on DPP-VIII. DPP-VIII in PBS (137 mM NaCl, 2.7 mM KCl, 1.4 mM KH$_2$PO$_4$, 4.3 mM Na$_2$HPO$_4$, pH 7.4) was incubated with 1 μl of the test compound in DMSO at 37° C. for 10 min. 0.5 μl of Gly-Pro-para-nitroanilide was added (final concentration: 2.5 mM). The resulting solution was incubated at 37° C. for 30-45 min. The reactions were monitored and measured at OD 405 nm. IC$_{50}$ values were calculated based on the results.

All test compounds exhibited low IC$_{50}$ values in inhibiting DPP-IV (either from human serum or from insect cells) and high $IC_{50}$ values in inhibiting DPP-VIII (from baculovirus-infected sfa cells). Some of the test compounds showed a very high ratio of the $IC_{50}$ value in inhibiting DPP-VIII to the $IC_{50}$ value in inhibiting DPP-IV, e.g., 100 or even higher. Thus, compounds 1-24 all have high selectivity in inhibiting DPP-VI over inhibiting DPP-VIII.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. For example, compounds structurally analogous to pyrrolidine compounds of this invention also can be made, screened for their inhibitory activities against DPP-IV and treating Type II diabetes and used to practice this invention. Thus, other embodiments are also within the claims.

What is claimed is:

1. A compound, wherein the compound is one of compounds 1-15 and 17-19 as shown below:

1

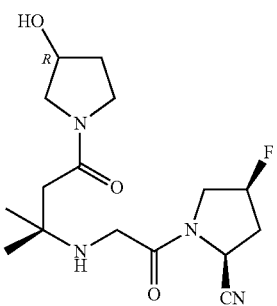

2

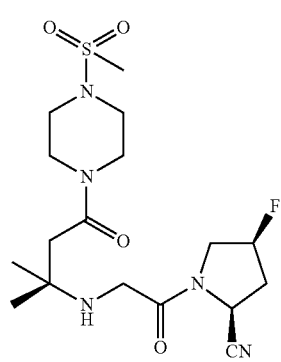

3

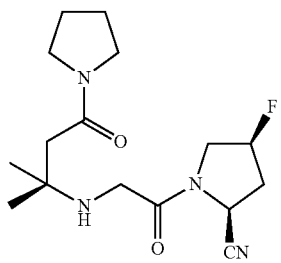

4

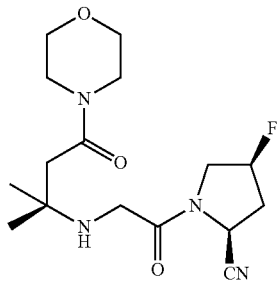

5

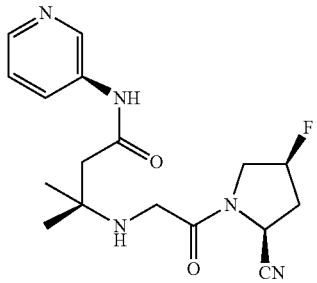

-continued

6

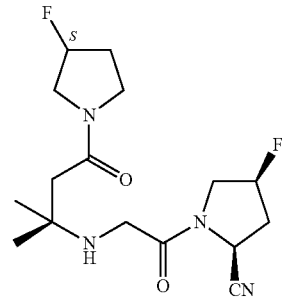

7

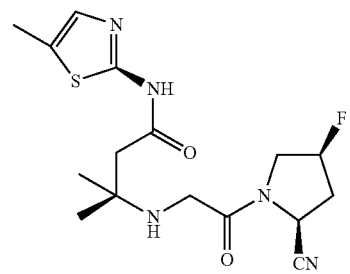

8

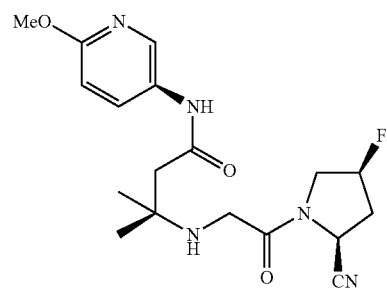

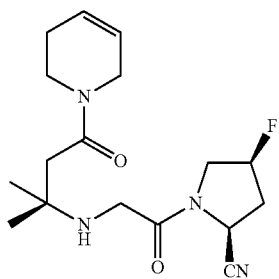
9
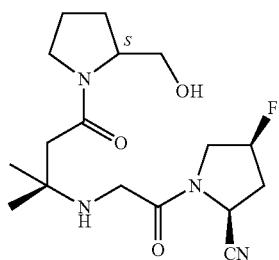
14
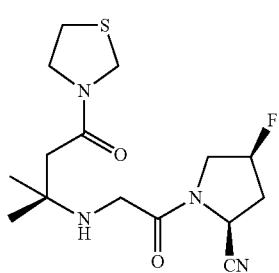
10
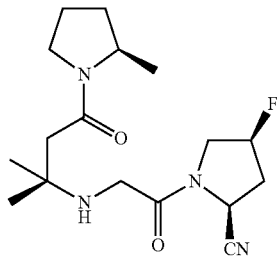
15
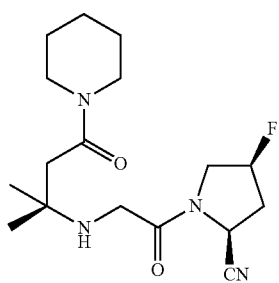
11
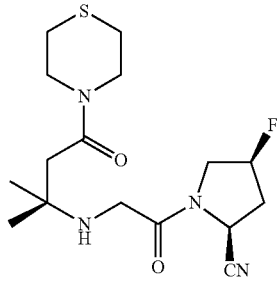
17
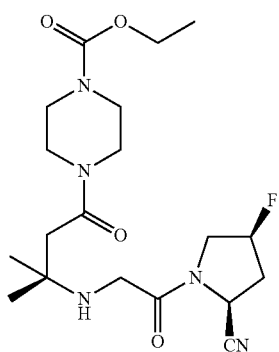
12
18
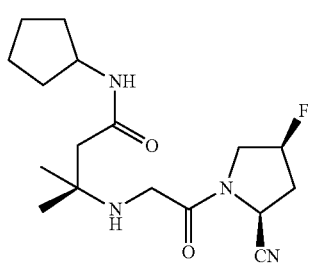
13
19
* * * * *